(12) United States Patent
Choi et al.

(10) Patent No.: US 9,420,954 B2
(45) Date of Patent: Aug. 23, 2016

(54) FIBER SCANNING OPTICAL PROBE AND MEDICAL IMAGING APPARATUS INCLUDING THE SAME

(71) Applicants: SAMSUNG ELECTRONICS CO., LTD., Suwon-si (KR); Korea Advanced Institute Of Science and Technology, Daejeon (KR)

(72) Inventors: Minseog Choi, Seoul (KR); Ki-Hun Jeong, Daejeon (KR); Hyeoncheol Park, Daejeon (KR); Seungwan Lee, Suwon-si (KR)

(73) Assignees: SAMSUNG ELECTRONICS CO., LTD., Suwon-si (KR); Korea Advanced Institute Of Science and Technology, Daejeon (KR)

( * ) Notice: Subject to any disclaimer, the term of this patent is extended or adjusted under 35 U.S.C. 154(b) by 0 days.

(21) Appl. No.: 13/920,533

(22) Filed: Jun. 18, 2013

(65) Prior Publication Data
US 2014/0005532 A1  Jan. 2, 2014

(30) Foreign Application Priority Data
Jun. 29, 2012  (KR) .................. 10-2012-0071413

(51) Int. Cl.
*A61B 5/00*  (2006.01)
(52) U.S. Cl.
CPC ............. *A61B 5/0095* (2013.01); *A61B 5/0066* (2013.01); *A61B 5/444* (2013.01); *A61B 5/72* (2013.01)

(58) Field of Classification Search
CPC .......... A61B 5/09; A61B 5/72; A61B 5/0095; A61B 5/0066; A61B 5/444; A61B 26/103
USPC .......................................... 600/425, 342, 478
See application file for complete search history.

(56) References Cited

U.S. PATENT DOCUMENTS

| | | |
|---|---|---|
| 6,975,898 B2 | 12/2005 | Seibel |
| 2004/0254474 A1 | 12/2004 | Seibel et al. |
| 2008/0221388 A1 | 9/2008 | Seibel et al. |
| 2010/0280534 A1* | 11/2010 | Sher .............................. 606/159 |

FOREIGN PATENT DOCUMENTS

KR  10-2004-0020864 A  3/2004

OTHER PUBLICATIONS

Wu, et al., "Two-dimensional scanning realized by an asymmetry fiber cantilever driven by single piezo bender actuator for optical coherence tomography." Aug. 3, 2009, Optics Express, vol. 17, No. 16, pp. 13819-13829.*

(Continued)

*Primary Examiner* — Long V Le
*Assistant Examiner* — Katherine McDonald
(74) *Attorney, Agent, or Firm* — Sughrue Mion, PLLC

(57) ABSTRACT

A fiber scanning optical probe including: an optical fiber; an actuator that drives the optical fiber in two directions; and an asymmetric structure that is disposed at one end of the optical fiber.

22 Claims, 7 Drawing Sheets

(56) References Cited

OTHER PUBLICATIONS

Min, et al., "Two-dimensional scanning probe driven by a solenoid-based single actuator for optical coherence tomography." Mar. 14, 2011, Optics Letters, vol. 36, No. 11, pp. 1963-1965.*

Roberts, et al., "1D and 2D laser line scan generation using a fibre optic resonant scanner." 2000, Micro-Opto-Electro-Mechanical Systems, Proceedings of SPIE, vol. 4075, pp. 62-73.*

* cited by examiner

FIBER SCANNING OPTICAL PROBE AND MEDICAL IMAGING APPARATUS INCLUDING THE SAME

CROSS-REFERENCE TO RELATED APPLICATION

This application claims the priority from Korean Patent Application No. 10-2012-0071413, filed on Jun. 29, 2012, in the Korean Intellectual Property Office, the disclosure of which is incorporated herein in its entirety by reference.

BACKGROUND

1. Field

Methods and apparatuses consistent with exemplary embodiments relate to fiber scanning optical probes and medical imaging apparatuses including the same.

2. Description of the Related Art

Technologies for performing precise tomography of lower layers of the human skin tissue are in high demand. Also, accurate information about the human skin tissue is required in medical imaging for medical diagnosis. In particular, since most cancers start in the lower cells of the epithelium and spread to cells of the hypodermis where blood vessels exist, if early stage cancer can be detected, damages caused by cancer can be greatly reduced. In existing imaging technologies, such as magnetic resonance imaging (MRI), x-ray computed tomography (CT), ultrasonography, and the like, tomography may be performed on layers inside the human skin tissue by penetrating the human skin tissue. However, since the resolutions of devices for such imaging technologies are low, early stage cancer, in which a tumor is small, might not be detected. On the other hand, in optical coherence tomography (OCT) technologies, optical coherence microscopy (OCM) technologies, and photoacoustic tomography (PAT) technologies that have been recently introduced, the penetration depths of light into skin are about 1 mm to about 2 mm (in the case of OCT) and about 30 mm to about 50 mm (in the case of PAT), and thus, are low compared to those of existing imaging methods. The resolutions of devices used in OCT technologies, OCM technologies, and PAT technologies are about 10 times those of ultrasound devices and thus are high compared to those of devices for performing other imaging methods. Thus, devices used in OCT technologies, OCM technologies, and PAT technologies are expected to be useful for early stage cancer diagnosis.

In order to apply these medical imaging technologies using light to diagnose inner parts of the human body by using endoscopy, laparoscopy, a surgical operation robot, or the like, light should be transferred from a light source to the inner parts of the human body. In this case, optical probes are used. Various scanning methods are used along with such optical probes, such as a method of using several bundles of optical fiber, a method of controlling an optical path by directly modifying an optical fiber, or a method of dividing an optical path by using a plurality of beam splitters, so as to obtain images of objects in predetermined regions.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide fiber scanning optical probes that may change a path of light by directly modifying an optical fiber and medical imaging apparatuses including the fiber scanning optical probes.

According to an aspect of an exemplary embodiment, there is provided a fiber scanning optical probe which includes: an optical fiber; an actuator that drives the optical fiber in two directions; and an asymmetric structure that is disposed at one end of the optical fiber.

The asymmetric structure may have a hole or groove into which the optical fiber is inserted.

The asymmetric structure may have a symmetric cross-section and non-uniform thickness. For example, the asymmetric structure may have a shape such that a part of a cylindrical top surface of a cylinder in which a through hole perforating a center of the cylinder is formed, is etched.

The asymmetric structure may have an asymmetric cross-section and uniform thickness. For example, a cross-sectional shape of the asymmetric structure may be a partially circular shape and a groove is formed in a center of the asymmetric structure. In this case, a central angle of the partially circular shape may be equal to or greater than about 180°.

The asymmetric structure may have a cylindrical shape and a through hole is formed eccentrically from a center of the asymmetric structure; the asymmetric structure may have a rectangular pillar shape and a through hole may be formed in a center of the asymmetric structure; the asymmetric structure may have a square pillar shape and a through hole may be formed eccentrically from a center of the asymmetric structure; the asymmetric structure may have an oval pillar shape and a through hole may be formed in a center of the asymmetric structure.

The asymmetric structure may be formed of silicon.

The fiber scanning optical probe may further include a probe body that forms an internal space in which the optical fiber, the actuator, and the asymmetric structure are accommodated and that comprises an optical input unit and an optical output unit.

A lens unit may include at least one lens is disposed in an optical path between the optical fiber and the optical output unit in the probe body.

The lens unit may include a graded index (GRIN) lens.

An optical path conversion member may be disposed between the lens unit and the optical output unit in the probe body and the optical path conversion member may include a reflection mirror; the optical path conversion member may include a prism.

According to an aspect of an exemplary embodiment, there is provided a medical imaging device which includes: a light source; a fiber scanning optical probe that scans an object to be imaged by irradiating light emitted from the light source onto the object; a receiver that receives a signal generated from the object; and a signal processor that generates an image signal by processing the signal received by the receiver.

The signal processor may process the received signal by using an OCT, an OCM, or a PAT.

BRIEF DESCRIPTION OF THE DRAWINGS

The above and/or other aspects will become more apparent by describing certain exemplary embodiments, with reference the accompanying drawings, in which.

DETAILED DESCRIPTION

Figure 1:
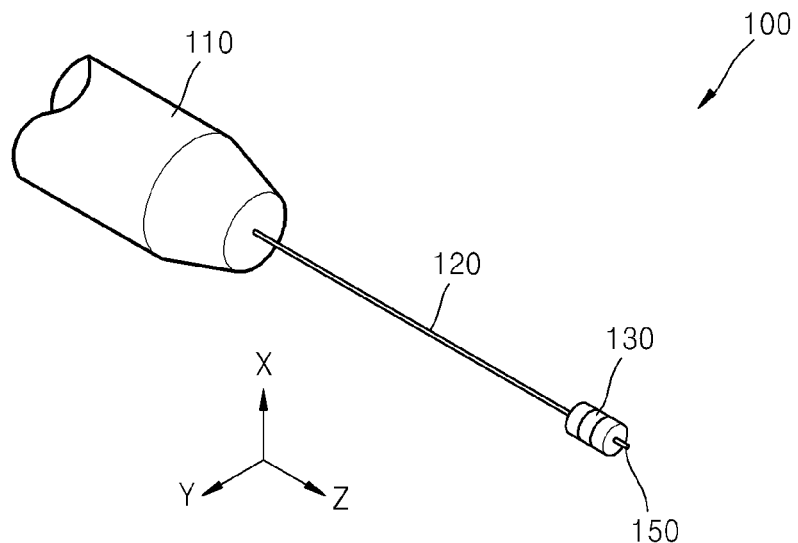
FIG. 1 illustrates a schematic structure of a fiber scanning optical probe according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 illustrates a schematic structure of a fiber scanning optical probe 100 according to an exemplary embodiment.

Referring to FIG. 1, the fiber scanning optical probe 100 includes an optical fiber 120, an actuator 110 that drives the optical fiber 120, and an asymmetric structure 130 that is disposed at one end 150 of the optical fiber 120.

The fiber scanning optical probe 100 uses a method of scanning light in a predetermined region by inducing modification of the optical fiber 120. To this end, the actuator 110 is configured to drive the optical fiber 120 in two directions so that an end of the optical fiber 120 may be modified in two directions, for example, in x- and y-directions. The actuator 110 may be a piezoelectric actuator that includes a piezoelectric material of which shape is modified according to an electric signal, for example.

The optical fiber 120 is driven by the actuator 110 and transfers light from an external light source to an object to be imaged. The optical fiber 120 may be a single mode optical fiber.

The asymmetric structure 130 separates resonant frequencies in two directions when the optical fiber 120 is driven. When a scanning operation is performed by driving the optical fiber 120, the actuator 110 drives the optical fiber 120 at a resonant frequency of a fiber-actuator system or in a frequency region that is adjacent to the resonant frequency in order to obtain the maximum efficiency. Hereinafter, the term 'fiber-actuator system' includes an actuator and all structures that are driven by the actuator, i.e., an optical fiber and an asymmetric structure coupled to the optical fiber. When the scanning operation is performed, if resonant frequencies of the fiber-actuator system in the two directions in which the optical fiber 120 is driven are the same, it is not easy to obtain a precise scanning path due to a 2-axis coupling effect. For example, a precise straight line path is not formed when the optical fiber 120 is driven in one direction. Since the resonant frequency of the fiber-actuator system is proportional to a bending inertial moment, resonant frequencies of the fiber-actuator system in the two directions may be different from each other, thereby making the bending moments in the two directions different from each other. In this regard, in the present exemplary embodiment, the resonant frequencies of the fiber-actuator system may be different from each other due to the asymmetric structure 130 having different bending moments in two directions at the optical fiber 120. The asymmetric structure 130 may include a hole or groove into which the optical fiber 120 is inserted so that the asymmetric structure 130 may be easily coupled with the actuator 110 as illustrated in FIG. 1. In addition, the asymmetric structure 130 may be formed of a proper material and may have a proper shape so as to adjust the resonant frequencies in the two directions to desired values. Although only one asymmetric structure 130 is shown in FIG. 1, a plurality of asymmetric structures 130 may be disposed in the fiber scanning optical probe 100.

Figure 2:
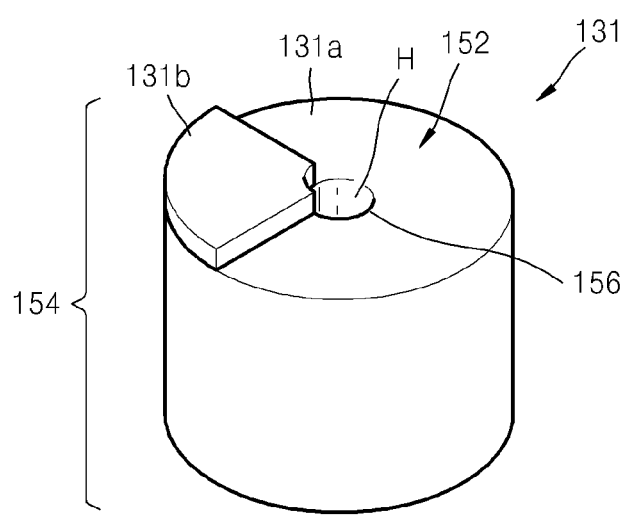
FIG. 2 illustrates an asymmetric structure that may be used in the fiber scanning optical probe of FIG. 1, according to an exemplary embodiment.

FIG. 2 illustrates an asymmetric structure 131 that may be used in the fiber scanning optical probe 100 of FIG. 1, according to an exemplary embodiment.

The asymmetric structure 131 has a shape such that a part of a top surface 152 of a cylinder 154 in which a through hole H perforating a central portion 156 of the cylinder is formed, is etched. That is, the asymmetric structure 131 has a shape in which a cut, sector-shaped pillar part 131b, i.e., a protrusion, protrudes from a cylinder part 131a in which the through hole H is formed. The angle or thickness of the cut, sector-shaped pillar part 131b may be determined in consideration of specific values of resonant frequencies in the two directions.

The asymmetric structure 131 of FIG. 2 may have a symmetric cross-section and non-uniform thickness so that bending moments in the two directions may be different from each other.

The asymmetric structure 131 of FIG. 2 may have an asymmetric cross-section and uniform thickness so that bending moments in the two directions may be different from each other. Hereinafter, FIGS. 3 through 7 illustrate examples of asymmetric structures 132, 133, 134, 135, and 136 that may be used in the fiber scanning optical fiber 100 of FIG. 1.

Figure 3:
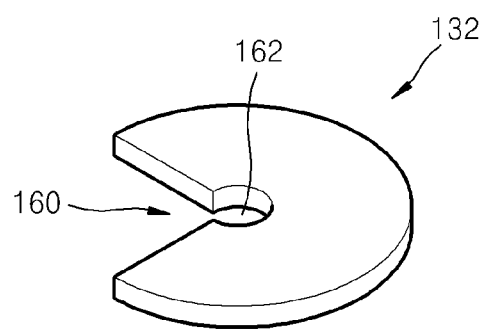
FIG. 3 illustrates an asymmetric structure that may be used in the fiber scanning optical probe of FIG. 1, according to an exemplary embodiment.

FIG. 3 illustrates the asymmetric structure 132 that may be used in the fiber scanning optical probe 100 of FIG. 1, according to another exemplary embodiment.

The cross-sectional shape of the asymmetric structure 132 is a partially circular shape in which a pie-like portion 160 is removed, and a groove 162 is formed in a central portion 156 of the asymmetric structure 132. The groove formed in the central portion of the asymmetric structure 132 is an area in which an optical fiber (see 120 of FIG. 1) is to be inserted. The asymmetric structure 132 may be stably installed on the optical fiber (see 120 of FIG. 1) by setting a central angle of the partially circular shape to equal to or greater than about 180°.

Figure 4:
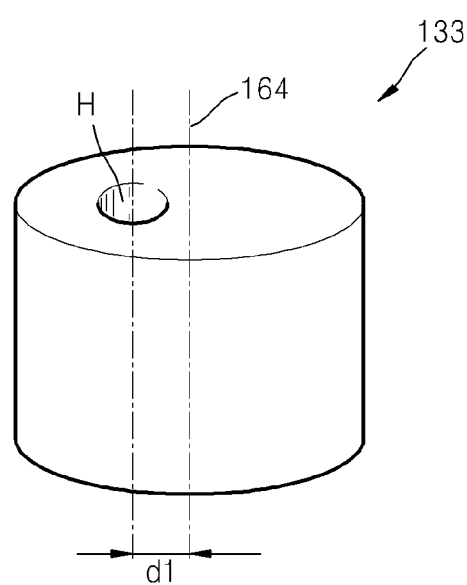
FIG. 4 illustrates an asymmetric structure that may be used in the fiber scanning optical probe of FIG. 1, according to an exemplary embodiment.
Figure 5:
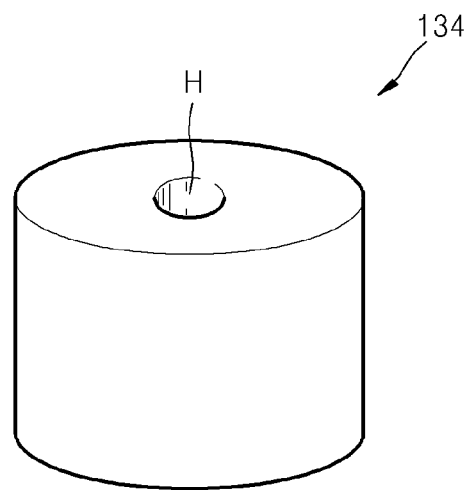
FIG. 5 illustrates an asymmetric structure that may be used in the fiber scanning optical probe of FIG. 1, according to an exemplary embodiment.
Figure 6:
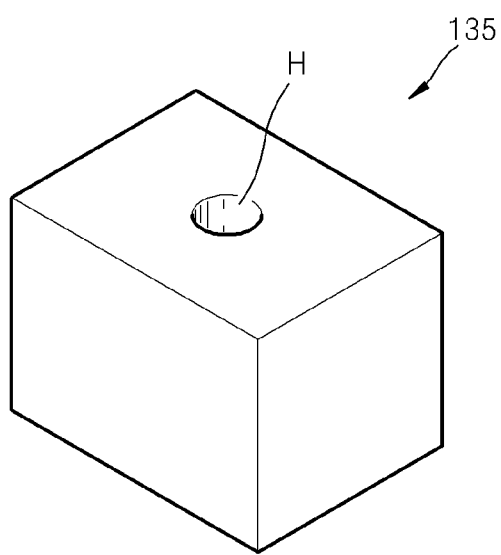
FIG. 6 illustrates an asymmetric structure that may be used in the fiber scanning optical probe of FIG. 1, according to an exemplary embodiment.
Figure 7:
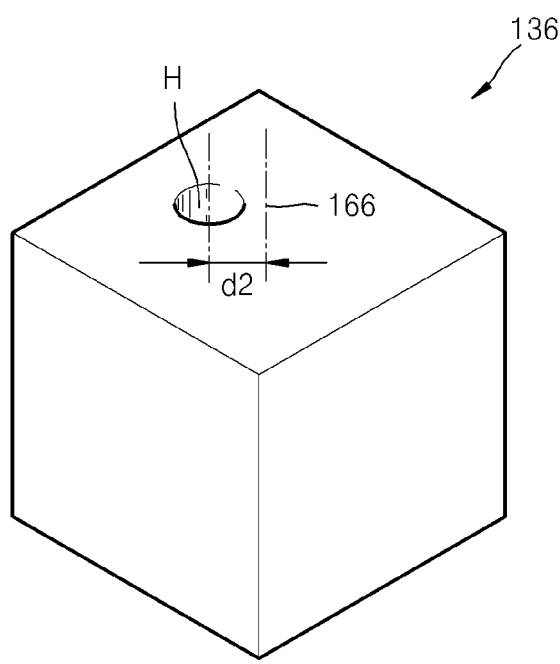
FIG. 7 illustrates an asymmetric structure that may be used in the fiber scanning optical probe of FIG. 1, according to an exemplary embodiment.

FIG. 4 illustrates the asymmetric structure 133 that may be used in the fiber scanning optical probe 100 of FIG. 1, according to an exemplary embodiment, FIG. 5 illustrates the asymmetric structure 134 that may be used in the fiber scanning optical probe 100 of FIG. 1, according to an exemplary, FIG. 6 illustrates the asymmetric structure 135 that may be used in the fiber scanning optical probe 100 of FIG. 1, according to an exemplary embodiment, and FIG. 7 illustrates the asymmetric structure 136 that may be used in the fiber scanning optical probe 100 of FIG. 1, according to an exemplary embodiment.

The asymmetric structure 133 of FIG. 4 has a cylindrical shape and through hole H is formed eccentrically with an offset from the central axis 164 of the asymmetric structure 133 by a distance d1.

The asymmetric structure 134 of FIG. 5 has an oval pillar shape with an oval cross-section and a through hole H is formed in a central portion 156 of the asymmetric structure 134.

The asymmetric structure 135 of FIG. 6 has a rectangular pillar shape with a rectangular cross-section in which a through hole H is formed in a central portion 156 of the asymmetric structure 135. The asymmetric structure 136 of FIG. 7 has a square pillar shape with a square cross-section in which a through hole H is formed with an offset from the central axis 166 of the asymmetric structure 136 by a distance d2.

The asymmetric structures 131, 132, 133, 134, 135, and 136 illustrated in FIGS. 2 through 7 may be formed of silicon and may be fabricated on a silicon substrate by performing a batch process.

Figure 8A:
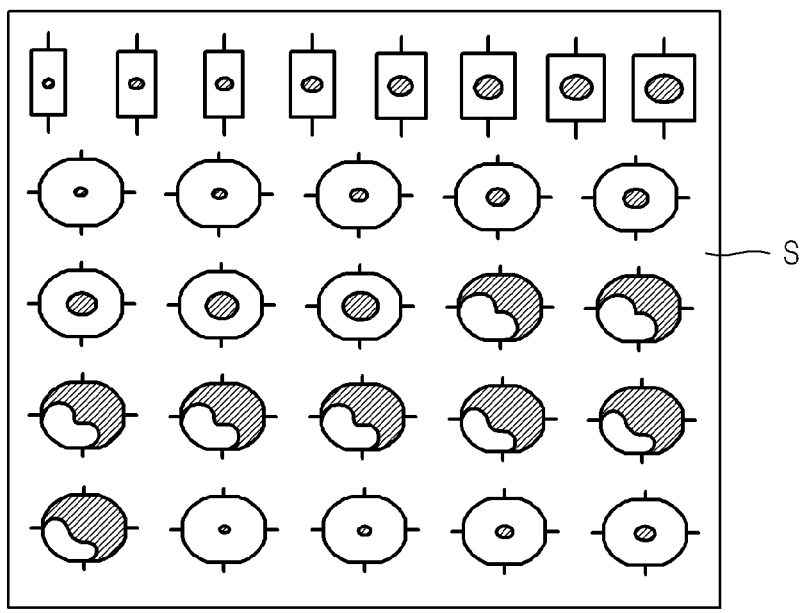
FIGS. 8A and 8B illustrate a method of fabricating an asymmetric structure that is used in the fiber scanning optical probe of FIG. 1.
Figure 8B:
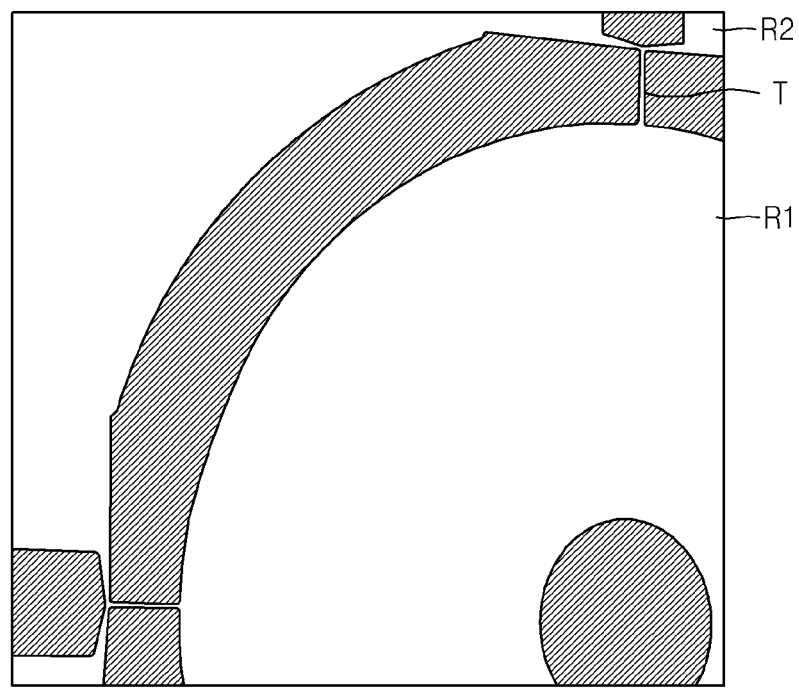

FIGS. 8A and 8B illustrate a method of fabricating an asymmetric structure that is used in the fiber scanning optical probe 100 of FIG. 1.

Referring to FIG. 8A, asymmetric structures having different shapes are fabricated on a silicon substrate S. The asymmetric structures may be fabricated by performing a microelectromechanical system (MEMS) process, such as a deep reactive ion etching (RIE) process. The asymmetric structures may have asymmetric shapes or may be formed to have non-uniform thicknesses by using partial etching, for example.

FIG. 8B is an enlarged view of a portion of FIG. 8A. In FIG. 8B, a substrate region R1 that forms the asymmetric structures, is connected to the other substrate region R2 via a connection part T having a thin band shape. The connection part T may be removed using mechanical shock or joule heating, for example. Thus, the asymmetric structures may be separated from the silicon substrate S.

Figure 9:
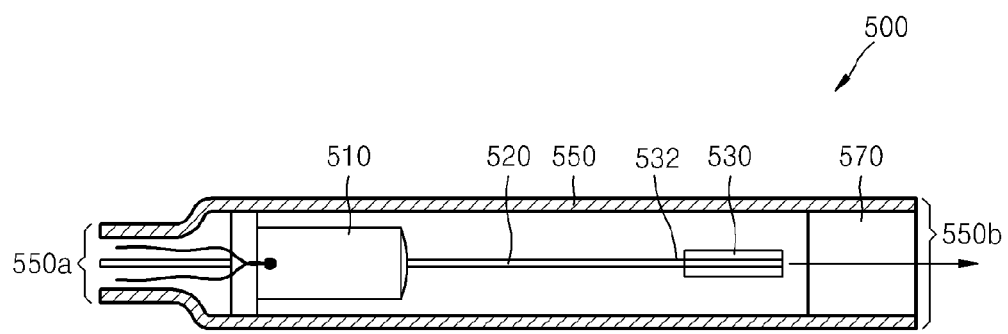
FIG. 9 illustrates a schematic structure of a fiber scanning optical probe according to an exemplary embodiment.

FIG. 9 illustrates a schematic structure of a fiber scanning optical probe 500 according to an exemplary embodiment.

Referring to FIG. 9, the fiber scanning optical probe 500 according to the present exemplary embodiment has a structure in which an actuator 510, an optical fiber 520, and an asymmetric structure 530 installed at one end 532 of the optical fiber 520 are accommodated in a probe body 550 including an optical input unit 550a and an optical output unit 550b.

The actuator 510 drives the optical fiber 520 along two axes and may be a piezoelectric actuator, for example. The asymmetric structure 530 separates 2-axis direction resonant frequencies of the fiber-actuator system and may include asymmetric structures 131, 132, 133, 134, 135, and 136 illustrated in FIGS. 2 through 7, or a combination structure thereof. A plurality of asymmetric structures 530 may be provided.

A lens unit 570 including at least one lens (not shown) may be disposed in an optical path between the optical fiber 520 and the optical output unit 550b. The lens unit 570 focuses light transferred via the optical fiber 520 on an object to be imaged. The lens unit 570 may include an optical lens formed of polymer or glass, or a graded index (GRIN) lens having a distribution of refractive index to focus light.

Figure 10:
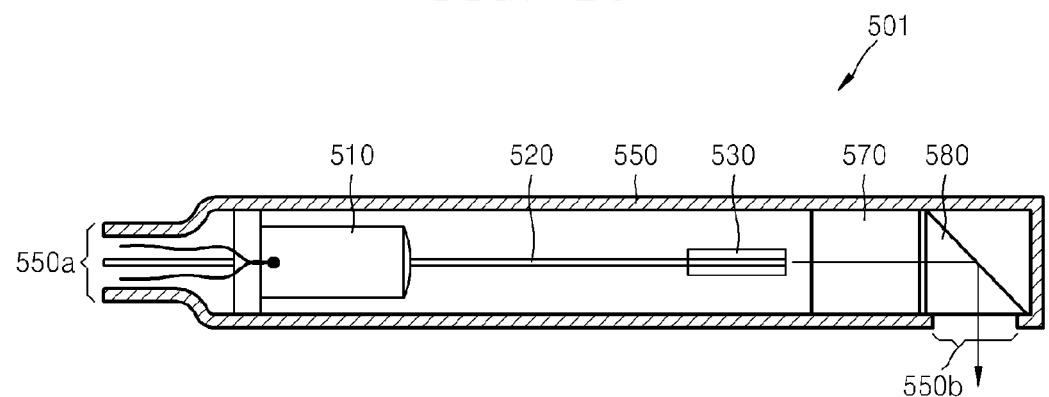
FIG. 10 illustrates a schematic structure of a fiber scanning optical probe according to an exemplary embodiment.

FIG. 10 illustrates a schematic structure of a fiber scanning optical probe 501 according to an exemplary embodiment.

The fiber scanning optical probe 501 of FIG. 10 is different from the fiber scanning optical probe 500 of FIG. 6 in that an optical path conversion member 580 is disposed between a lens unit 570 and an optical output unit 550b in a probe body 550. The optical path conversion member 580 may have a shape of a prism, as illustrated in FIG. 10, and an optical path is converted by total reflection on a prism plane.

Figure 11:
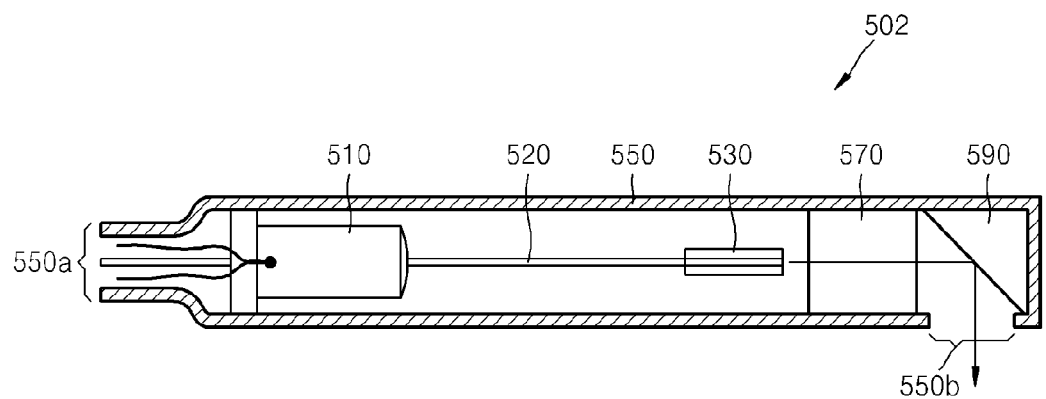
FIG. 11 illustrates a schematic structure of a fiber scanning optical probe according to an exemplary embodiment.

FIG. 11 illustrates a schematic structure of a fiber scanning optical probe 502 according to an exemplary embodiment.

The fiber scanning optical probe 502 is different from the fiber scanning optical probe 501 of FIG. 7 in that an optical path conversion member 580 includes a reflection mirror.

The fiber scanning optical probes 100, 500, 501, and 502 illustrated in FIG. 1 and FIGS. 9 through 11 have resonant frequencies that vary according to their driving directions. Thus, coupling between axes is prevented so that more precise optical scanning can be performed. In addition, the above-described fiber scanning optical probes 100, 500, 501, and 502 illustrated in FIG. 1 and FIGS. 9 through 11 may be used in medical imaging devices to reduce cross-talk and provide medical images having improved quality.

Figure 12:
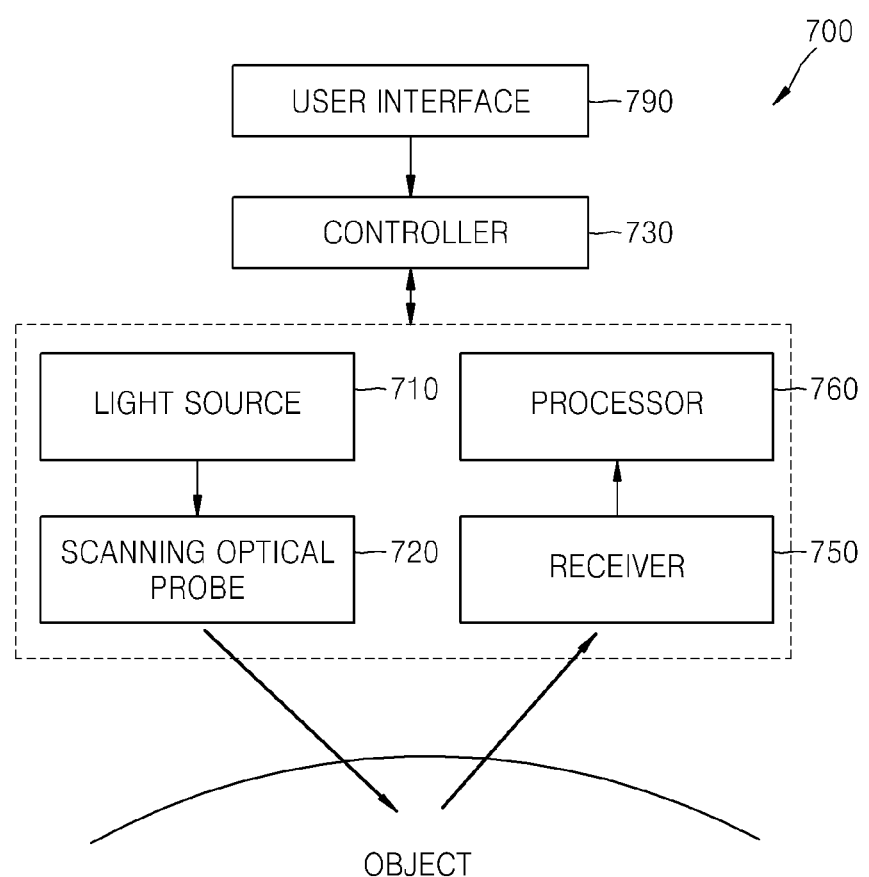
FIG. 12 is a block diagram of a schematic structure of a medical imaging apparatus according to an exemplary embodiment.

FIG. 12 is a block diagram of a schematic structure of a medical imaging apparatus 700 according to an exemplary embodiment.

The medical imaging apparatus 700 includes a light source 710, a scanning optical probe 720 that scans an object to be imaged by irradiating light emitted from the light source 710 onto the object, a receiver 750 that receives a signal generated from the object, and a signal processor 760 that generates an image signal by processing the signal received from the receiver 750.

The scanning optical probe 720 has a configuration in which a predetermined region of the object is scanned by the light irradiated thereto. For example, the scanning optical probe 720 may include one of the fiber scanning optical probes 100, 500, 501, and 502 illustrated in FIG. 1 and FIGS. 9 through 11, or a combination thereof.

When light is irradiated onto the object via the scanning optical probe 720, a new signal including information regarding characteristics of the object is formed, and the receiver 750 receives the signal. The receiver 750 may be included in the scanning optical probe 720.

The signal processor 760 generates an image signal by processing the signal received by the receiver 750.

In addition, the medical imaging apparatus 700 may further include a user interface 790 and a controller 730. The user interface 790 may include an input unit and a display and may transmit an input to the controller 730 by using the input unit and the display.

The controller 730 controls elements of the medical imaging apparatus 700 in response to a command input from the user interface 790. For example, the controller 730 may control driving of the scanning optical probe 720. The controller 730 may be implemented with a microprocessor, or the like.

The medical imaging apparatus 700 may use methods such as an OCT, OCM, PAT, and the like. For example, a detection sensor that is disposed on the receiver 750, may vary according to a type of a signal generated in the object, and the signal processing unit 760 may process the received signal by using one of the methods.

For example, when the medical imaging apparatus 700 uses PAT, the light source 710 may be a pulse laser that induces ultrasonic waves from the object and the receiver 750 may be an ultrasound receiver that includes a transducer for transforming ultrasonic waves generated from the object into electric signals.

Although a few exemplary embodiments have been shown and described, exemplary embodiments are not limited thereto. Instead, it would be appreciated by those skilled in the art that changes may be made to these exemplary embodiments without departing from the principles and spirit of the disclosure, the scope of which is defined by the claims and their equivalents.

What is claimed is:

1. A fiber scanning optical probe comprising:
    an optical fiber comprising an elongated body which comprises a first end and a second end and extends in a free space between the first end and the second end;
    an actuator that drives the optical fiber in two directions and is disposed at the second end; and
    an asymmetric structure that is disposed at the first end opposite the actuator and comprises:
        a first surface and a second surface disposed opposing one another, and
        a body through which the optical fiber extends and which comprises a side surface which is disposed between the first surface and the second surface substantially parallel to the optical fiber,
        wherein the asymmetric structure is shaped such that the optical fiber with the asymmetric structure has different bending inertial moment in the two directions.

2. The fiber scanning optical probe of claim 1, wherein the asymmetric structure has a hole or a groove into which the optical fiber is inserted.

3. The fiber scanning optical probe of claim 1, wherein the asymmetric structure has a symmetric cross-section and non-uniform thickness.

4. The fiber scanning optical probe of claim 3, wherein the asymmetric structure has a shape of a cylinder in which a hole perforating a central portion of the cylinder is formed, and one of the first surface and the second surface is etched.

5. The fiber scanning optical probe of claim 1, wherein the asymmetric structure has an asymmetric cross-section and uniform thickness.

6. The fiber scanning optical probe of claim 5, wherein a cross-sectional shape of the asymmetric structure is a partially circular shape and a groove is formed in a central portion of the asymmetric structure.

7. The fiber scanning optical probe of claim 6, wherein a central angle of the partially circular shape is equal to or greater than about 180°.

8. The fiber scanning optical probe of claim 5, wherein the asymmetric structure has a cylindrical shape and a through hole is offset from a center of the asymmetric structure.

9. The fiber scanning optical probe of claim 5, wherein the asymmetric structure has a rectangular pillar shape and a through hole is formed in a central portion of the asymmetric structure.

10. The fiber scanning optical probe of claim 5, wherein the asymmetric structure has a square pillar shape and a through hole is offset from a center of the asymmetric structure.

11. The fiber scanning optical probe of claim 5, wherein the asymmetric structure has an oval pillar shape and a through hole is formed in a central portion of the asymmetric structure.

12. The fiber scanning optical probe of claim 1, wherein the asymmetric structure is formed of silicon.

13. The fiber scanning optical probe of claim 1, further comprising:
    a probe body that forms an internal space in which the optical fiber, the actuator, and the asymmetric structure are accommodated,
    wherein the optical fiber is disposed between an optical input and an optical output.

14. The fiber scanning optical probe of claim 13, wherein a lens unit comprising a lens is disposed in an optical path between the optical fiber and the optical output, in the probe body.

15. The fiber scanning optical probe of claim 14, wherein the lens unit comprises a graded index (GRIN) lens.

16. The fiber scanning optical probe of claim 14, wherein an optical path conversion member is disposed between the lens unit and the optical output, in the probe body.

17. The fiber scanning optical probe of claim 16, wherein the optical path conversion member comprises a reflection mirror.

18. The fiber scanning optical probe of claim 16, wherein the optical path conversion member comprises a prism.

19. A medical imaging device comprising:
    a light source;
    a fiber scanning optical probe that scans an object to be imaged by irradiating light emitted from the light source onto the object;
    a receiver that receives a signal generated from the object; and
    a signal processor that generates an image signal by processing the signal received by the receiver,
    wherein the fiber scanning optical probe comprises:
    an optical fiber comprising an elongated body which comprises a first end and a second end and extends in a free space between the first end and the second end;
    an actuator that drives the optical fiber in two directions and is disposed at the second end; and
    an asymmetric structure that is disposed at the first end opposite the actuator and comprises:
        a first surface and a second surface disposed opposing one another, and
        a body through which the optical fiber extends and which comprises a side surface which is disposed between the first surface and the second surface substantially parallel to the optical fiber,
        wherein the asymmetric structure is shaped such that the optical fiber with the asymmetric structure has different bending inertial moment in the two directions.

20. The medical imaging device of claim 19, wherein the signal processor processes the received signal by using at least one of an optical coherence tomography (OCT), an optical coherence microscopy (OCM), or a photoacoustic tomography (PAT).

21. The fiber scanning optical probe of claim 1, wherein one of the first surface and the second surface comprises a protrusion extending a lengthwise direction of the body of the asymmetric structure.

22. The fiber scanning optical probe of claim 1, wherein an entire length of the optical fiber between the first end, at which the asymmetric structure is disposed, and the second end, at which the actuator is disposed, extends in the free space.

* * * * *